(12) United States Patent
Lee et al.

(10) Patent No.: US 10,112,050 B2
(45) Date of Patent: Oct. 30, 2018

(54) ELECTRODE SELECTION FOR SUB-THRESHOLD MODULATION THERAPY

(71) Applicant: Boston Scientific Neuromodulation Corporation, Valencia, CA (US)

(72) Inventors: Dongchul Lee, Agua Dulce, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 23 days.

(21) Appl. No.: 15/481,237

(22) Filed: Apr. 6, 2017

(65) Prior Publication Data

US 2017/0209702 A1    Jul. 27, 2017

Related U.S. Application Data

(63) Continuation of application No. 14/316,538, filed on Jun. 26, 2014, now Pat. No. 9,623,250.

(60) Provisional application No. 61/841,216, filed on Jun. 28, 2013.

(51) Int. Cl.
*A61N 1/36* (2006.01)
*A61N 1/372* (2006.01)

(52) U.S. Cl.
CPC ..... *A61N 1/36164* (2013.01); *A61N 1/36071* (2013.01); *A61N 1/36132* (2013.01); *A61N 1/36139* (2013.01); *A61N 1/36178* (2013.01); *A61N 1/36185* (2013.01); *A61N 1/37247* (2013.01)

(58) Field of Classification Search
CPC ............ A61N 1/36164; A61N 1/37247; A61N 1/36071; A61N 1/36185; A61N 1/36178

USPC ..................................................... 607/46, 59
See application file for complete search history.

(56) References Cited

U.S. PATENT DOCUMENTS

| | | | |
|---|---|---|---|
| 6,393,325 B1 | 5/2002 | Mann et al. | |
| 6,516,227 B1 | 2/2003 | Meadows et al. | |
| 6,675,046 B2 | 1/2004 | Holsheimer | |
| 6,895,280 B2 | 5/2005 | Meadows et al. | |
| 6,993,384 B2 | 1/2006 | Bradley et al. | |

(Continued)

FOREIGN PATENT DOCUMENTS

| | | |
|---|---|---|
| CN | 102438698 A | 5/2012 |
| CN | 103002947 A | 3/2013 |

(Continued)

OTHER PUBLICATIONS

"U.S. Appl. No. 14/316,538, Non Final Office Action dated Jul. 13, 2016", 9 pgs.

(Continued)

*Primary Examiner* — Christopher D Koharski
*Assistant Examiner* — Roland Dinga
(74) *Attorney, Agent, or Firm* — Schwegman Lundberg & Woessner, P.A.

(57) ABSTRACT

A neuromodulation system and method of providing sub-threshold therapy to a patient. An anodic perception threshold of super-threshold electrical energy and a cathodic perception threshold of super-threshold electrical energy are determined for a plurality of electrode sets. A ratio between the anodic perception threshold and the cathodic perception threshold is calculated for each of the electrode sets. An effective electrode set is selected based on the ratio between the anodic perception threshold and the cathodic perception threshold.

20 Claims, 13 Drawing Sheets

(56) References Cited

U.S. PATENT DOCUMENTS

| | | |
|---|---|---|
| 7,317,948 B1 | 1/2008 | King et al. |
| 7,333,857 B2 | 2/2008 | Campbell |
| 7,539,538 B2 | 5/2009 | Parramon et al. |
| 7,650,184 B2 | 1/2010 | Walter |
| 7,979,133 B2 | 7/2011 | Feler et al. |
| 8,019,439 B2 | 9/2011 | Kuzma et al. |
| 8,224,453 B2 | 7/2012 | De Ridder |
| 8,255,057 B2 | 8/2012 | Fang et al. |
| 8,332,039 B1 | 12/2012 | Huynh et al. |
| 8,355,797 B2 | 1/2013 | Caparso et al. |
| 8,380,318 B2 | 2/2013 | Kishawi et al. |
| 8,455,716 B2 | 6/2013 | Huang et al. |
| 8,504,147 B2 | 8/2013 | Deem et al. |
| 8,615,300 B2 | 12/2013 | Feler et al. |
| 8,649,874 B2 | 2/2014 | Alataris et al. |
| 8,670,831 B2 | 3/2014 | Wacnik et al. |
| 8,676,329 B2 | 3/2014 | Wacnik et al. |
| 8,676,331 B2 | 3/2014 | Parker |
| 8,731,675 B2 | 5/2014 | Ranu et al. |
| 8,751,009 B2 | 6/2014 | Wacnik |
| 9,504,838 B2 | 11/2016 | Rao |
| 9,623,250 B2 | 4/2017 | Lee et al. |
| 2003/0139781 A1 | 7/2003 | Bradley et al. |
| 2007/0150036 A1 | 6/2007 | Anderson |
| 2008/0188909 A1 | 8/2008 | Bradley |
| 2008/0215119 A1 | 9/2008 | Woods et al. |
| 2009/0204173 A1 | 8/2009 | Fang et al. |
| 2010/0010566 A1 | 1/2010 | Thacker et al. |
| 2010/0121409 A1 | 5/2010 | Kothandaraman et al. |
| 2010/0249875 A1 | 9/2010 | Kishawi et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2010/0331926 A1* | 12/2010 | Lee ............... A61N 1/36071 607/72 |
| 2012/0059446 A1 | 3/2012 | Wallace et al. |
| 2012/0083709 A1 | 4/2012 | Parker et al. |
| 2012/0253422 A1 | 10/2012 | Thacker et al. |
| 2012/0265279 A1 | 10/2012 | Zhu et al. |
| 2012/0283797 A1 | 11/2012 | De Ridder |
| 2012/0290041 A1 | 11/2012 | Kim et al. |
| 2013/0066411 A1 | 3/2013 | Thacker et al. |
| 2013/0116752 A1 | 5/2013 | Parker et al. |
| 2013/0268021 A1 | 10/2013 | Moffitt |
| 2013/0296975 A1 | 11/2013 | Lee et al. |
| 2014/0081349 A1 | 3/2014 | Lee |
| 2014/0243926 A1 | 8/2014 | Carcieri |
| 2014/0277267 A1 | 9/2014 | Vansickle et al. |
| 2014/0364920 A1* | 12/2014 | Doan ............... A61N 1/36164 607/46 |
| 2015/0005842 A1 | 1/2015 | Lee et al. |

FOREIGN PATENT DOCUMENTS

| | | |
|---|---|---|
| CN | 105358214 A | 2/2016 |
| EP | 2529789 A1 | 12/2012 |
| EP | 2540340 A1 | 1/2013 |
| JP | 2016523175 A | 8/2016 |
| WO | WO-2006029257 A2 | 3/2006 |
| WO | WO-2006135791 A2 | 12/2006 |
| WO | WO-2014210373 A1 | 12/2014 |

OTHER PUBLICATIONS

"U.S. Appl. No. 14/316,538, Notice of Allowance dated Dec. 15, 2016", 9 pgs.

"U.S. Appl. No. 14/316,538, Response filed Oct. 12, 2016 to Non Final Office Action dated Jul. 13, 2016", 7 pgs.

"International Application Serial No. PCT/US2014/044430, International Preliminary Report on Patentability dated Jan. 7, 2016", 8 pgs.

"International Application Serial No. PCT/US2014/044430, International Search Report dated Sep. 19, 2014", 4 pgs.

"International Application Serial No. PCT/US2014/044430, Written Opinion dated Sep. 19, 2014", 6 pgs.

* cited by examiner

ELECTRODE SELECTION FOR SUB-THRESHOLD MODULATION THERAPY

CLAIM OF PRIORITY

This application is a continuation of U.S. application Ser. No. 14/316,538, filed Jun. 26, 2014, which claims the benefit of priority under 35 U.S.C. § 119(e) of U.S. Provisional Patent Application Ser. No. 61/841,216, filed on Jun. 28, 2013, each of which is herein incorporated by reference in its entirety.

FIELD OF THE INVENTION

The present inventions relate to tissue modulation systems, and more particularly, to programmable neuromodulation systems.

BACKGROUND

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

Each of these implantable neuromodulation systems typically includes at least one neuromodulation lead implanted at the desired modulation site and an Implantable Pulse Generator (IPG) implanted remotely from the modulation site, but coupled either directly to the neuromodulation lead(s), or indirectly to the neuromodulation lead(s) via one or more lead extensions. Thus, electrical pulses can be delivered from the neuromodulator to the electrodes carried by the neuromodulation lead(s) to stimulate or activate a volume of tissue in accordance with a set of modulation parameters and provide the desired efficacious therapy to the patient. The neuromodulation system may further comprise a handheld remote control (RC) to remotely instruct the neuromodulator to generate electrical modulation pulses in accordance with selected modulation parameters. The RC may, itself, be programmed by a technician attending the patient, for example, by using a Clinician's Programmer (CP), which typically includes a general purpose computer, such as a laptop, with a programming software package installed thereon.

Electrical modulation energy may be delivered from the neuromodulation device to the electrodes in the form of an electrical pulsed waveform. Thus, electrical modulation energy may be controllably delivered to the electrodes to modulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, width, and rate of the electrical pulses provided through the electrode array. Each electrode configuration, along with the electrical pulse parameters, can be referred to as a "modulation parameter set."

With some neuromodulation systems, and in particular, those with independently controlled current or voltage sources, the distribution of the current to the electrodes (including the case of the neuromodulation device, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neuromodulation device to generate electrical pulses in accordance with the selected modulation parameters. Typically, the modulation parameters programmed into the neuromodulation device can be adjusted by manipulating controls on the external control device to modify the electrical modulation energy delivered by the neuromodulation device system to the patient. Thus, in accordance with the modulation parameters programmed by the external control device, electrical pulses can be delivered from the neuromodulation device to the electrode(s) to modulate a volume of tissue in accordance with the set of modulation parameters and provide the desired efficacious therapy to the patient. The best modulation parameter set will typically be one that delivers electrical energy to the volume of tissue that must be modulate in order to provide the therapeutic benefit (e.g., treatment of pain), while minimizing the volume of non-target tissue that is modulated.

However, the number of electrodes available combined with the ability to generate a variety of complex electrical pulses, presents a huge selection of modulation parameter sets to the clinician or patient. For example, if the neuromodulation system to be programmed has an array of sixteen electrodes, millions of modulation parameter sets may be available for programming into the neuromodulation system. Today, neuromodulation system may have up to thirty-two electrodes, thereby exponentially increasing the number of modulation parameters sets available for programming.

To facilitate such selection, the clinician generally programs the neuromodulation device through a computerized programming system. This programming system can be a self-contained hardware/software system, or can be defined predominantly by software running on a standard personal computer (PC). The PC or custom hardware may actively control the characteristics of the electrical pulses generated by the neuromodulation device to allow the optimum modulation parameters to be determined based on patient feedback or other means and to subsequently program the neuromodulation device with the optimum modulation parameter set or sets. The computerized programming system may be operated by a clinician attending the patient in several scenarios.

For example, in order to achieve an effective result from conventional SCS, the lead or leads must be placed in a location, such that the electrical modulation (and in this case, electrical modulation) will cause paresthesia. The paresthesia induced by the electrical modulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When leads are implanted within the patient, the computerized programming system, in the context of an operating room (OR) mapping procedure, may be used to instruct the neuromodulation device to apply electrical modulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neuromodulation device, with a set of modulation parameters that best addresses the painful site. Thus, the navigation session may be used to pinpoint the volume of activation (VOA) or areas correlating to the pain. Such programming ability is particularly advantageous for targeting the tissue during implantation, or after implantation should the leads gradually or unexpectedly move that would otherwise relocate the modulation energy away from the target site. By reprogramming the neuromodulation device (typically by independently varying the modulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

Although alternative or artifactual sensations are usually tolerated relative to the sensation of pain, patients sometimes report these sensations to be uncomfortable, and therefore, they can be considered an adverse side-effect to neuromodulation therapy in some cases. Because the perception of paresthesia has been used as an indicator that the applied electrical energy is, in fact, alleviating the pain experienced by the patient, the amplitude of the applied electrical energy is generally adjusted to a level that causes the perception of paresthesia. It has been shown, however, that the delivery of sub-threshold electrical energy (e.g., high-rate pulsed electrical energy and/or low pulse width electrical energy) can be effective in providing neuromodulation therapy for chronic pain without causing paresthesia.

Although sub-threshold modulation therapies have shown good efficacy in early studies, because there is a lack of paresthesia that may otherwise indicate that the neuromodulation therapy is effective, it is difficult to immediately determine if the delivered sub-threshold therapy is optimized in terms of providing efficacious therapy to the patient. Given the lack of paresthesia, the clinician may have to try infinite combinations of electrodes, and modulation parameters of those electrodes to arrive at an optimal sub-threshold therapy program. Thus, identifying an efficacious sub-threshold therapy program may take several days, if not weeks, requiring several reprogramming sessions with the clinicians.

Thus, there remains a need to provide a means to ensure that a patient is being effectively treated using electrical sub-threshold therapy.

SUMMARY OF THE INVENTION

In accordance with a first aspect of the present inventions, a method of providing sub-threshold modulation therapy to a patient is provided. The method comprises determining an anodic perception threshold of super-threshold electrical energy respectively delivered from each of a plurality of electrode sets to the patient, determining a cathodic perception threshold of the super-threshold electrical energy respectively delivered from each of the electrode sets to the patient, calculating a ratio between the anodic perception threshold and the cathodic perception threshold for each of the electrode sets, selecting one of the electrode sets as an effective electrode set based on the ratios, and delivering sub-threshold electrical energy from the effective electrode set to the patient, thereby providing therapy to the patient. The sub-threshold level may be referred to as a patient-perception threshold, which may be referred to as a boundary below which a patient does not sense delivery of the electrical energy and at or above which the patient does sense delivery of the electrical energy. For example, in a spinal cord modulation system, the patient-perception threshold may be a boundary below which a patient does not experience paresthesia. The electrode set with the ratio between the anodic perception threshold and the cathodic perception threshold closest to unity may be selected as the effective electrode set.

Given a patient that suffers from pain in a body region, the method may also include creating a paresthesia map comprising a body region of perceived paresthesia resulting from the delivery of the super-threshold electrical energy from each of the electrode sets, and selecting the one electrode set as the effective electrode set based on the paresthesia map. In one method, the electrode set corresponding to the body region of perceived paresthesia that matches the body region of pain is selected as the effective electrode set. The method may also include generating a coverage score of a relative match between each body region of perceived paresthesia and the body region of pain, and the one electrode set that is selected as the effective electrode set is based on the coverage score.

Another method comprises computing a total score from the ratio of the anodic perception threshold and the cathodic perception threshold, and the coverage score for each of the electrode sets, and selecting as the effective electrode set the one electrode set having a highest total score.

The delivered sub-threshold electrical energy has a frequency greater than 1500 Hz, and a pulse duration lower than 200 µs. The delivered sub-threshold electrical energy may comprise an electrical pulse train. The electrical pulse train may be a biphasic pulse train. The biphasic pulse train may have an active anodic phase and a passive cathodic recharge phase.

Yet another method comprises selecting another one of the electrode sets as another effective electrode set based on the ratios, and delivering sub-threshold electrical energy from the other effective electrode set to the patient to provide therapy to the patient. The method also comprises distributing the electrical energy among the effective electrode sets based on a ratio between the anodic perception thresholds and/or the cathodic perception thresholds of the effective electrode sets.

In accordance with a second aspect of the present inventions, a neuromodulation system for use with a patient is provided. The neuromodulation system comprises a plurality of electrical terminals configured for being respectively coupled to a plurality of electrode sets, modulation output circuitry configured for independently super-threshold anodic electrical energy and super-threshold cathodic electrical energy from each of the electrode sets via the electrical terminals to the patient, and for delivering sub-threshold electrical energy from an effective one of the electrode sets via the electrical terminals to the patient, memory configured for storing an anodic perception threshold of the super-threshold anodic electrical energy respectively delivered from each of the electrode sets to the patient, and storing a cathodic perception threshold of the super-threshold cathodic electrical energy respectively delivered from each of the electrode sets to the patient, and control circuitry configured for computing a ratio between the anodic perception threshold and the cathodic perception threshold for each of the electrode sets, and selecting one of the electrode sets as the effective electrode set from which the modulation output circuitry delivers sub-threshold electrical energy to the patient based on the computed ratios.

In one embodiment, the neuromodulation system further comprises a user interface configured for receiving input from a user, wherein the control circuitry is configured for storing the anodic perception thresholds and cathodic perception thresholds in response to the user input. In another embodiment, the neuromodulation system comprises monitoring circuitry configured for sensing evoked compound action potentials (eCAPs) in the patient in response to the delivery of the super-threshold anodic electrical energy and the super-threshold cathodic electrical energy from each of the electrode sets to the patient. In this embodiment, the control circuitry is configured for storing the anodic perception threshold and cathodic perception threshold in response to the sensing of the eCAPs by the monitoring circuitry.

In one embodiment, the control circuitry is configured for automatically selecting the one electrode set as the effective set without input from the user. In another embodiment, the control circuitry is configured for automatically selecting a plurality of candidate electrode sets from the plurality of electrode sets based on the computed ratios through a user interface that is configured for displaying the candidate electrode sets to the user, and receiving input from the user. In response to the user input, the control circuitry is further configured for selecting one of candidate electrode sets as the effective electrode sets.

The control circuitry may be configured for selecting the electrode set with the ratio between the anodic perception threshold and the cathodic perception threshold closest to unity as the effective electrode set.

The control circuitry may also be configured for creating a paresthesia map comprising a body region of perceived paresthesia resulting from the delivery of the super-threshold electrical energy from each of the electrode sets, and for selecting the one electrode set as the effective electrode set based on the paresthesia map. The control circuitry may be configured for selecting the electrode set corresponding to the body region of paresthesia that matches a body region of pain as the effective electrode set.

In one embodiment, the control circuitry is configured for computing a coverage score of a relative match between each body region of perceived paresthesia and the body region of pain, and for selecting the one electrode set as the effective electrode set based on the coverage score. In another embodiment, the control circuitry is configured for computing a total score from the ratio and the coverage score for each of the electrode sets, and for selecting the one electrode set having a highest total score as the effective electrode set.

In yet another embodiment, the control circuitry is configured for selecting another one of the electrode sets as another effective electrode set based on the ratios, and the modulation output circuitry is configured for delivering sub-threshold electrical energy from the other effective electrode set to the patient. The control circuitry may also be configured for computing a distribution of the sub-threshold electrical energy among the effective electrode sets based on a ratio between the anodic perception thresholds and/or the cathodic perception thresholds of the effective electrode sets.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord modulation (SCM) system. However, it is to be understood that the while the invention lends itself well to applications in SCM, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
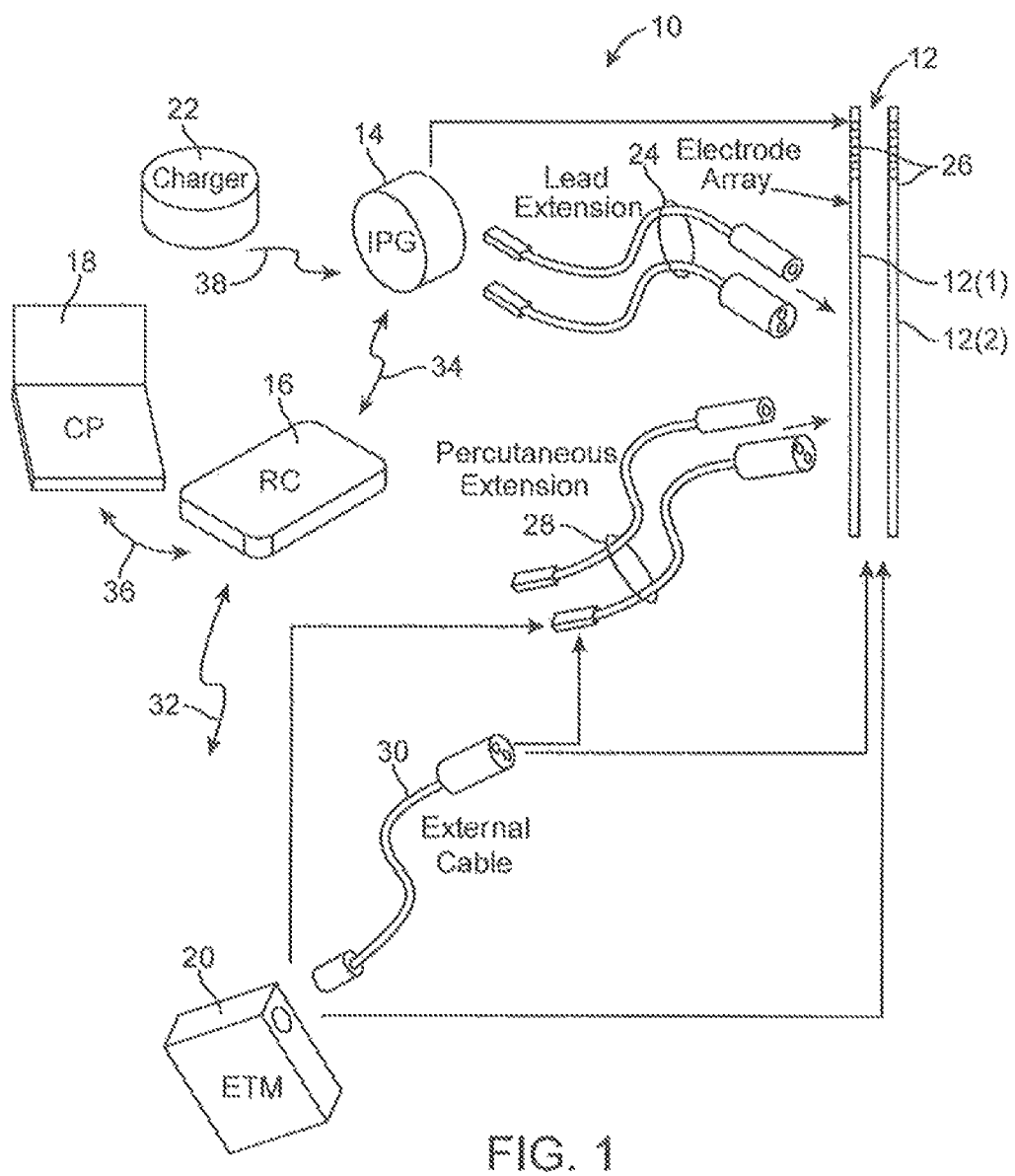
FIG. 1 is a plan view of a Spinal Cord Modulation (SCM) system constructed in accordance with one embodiment of the present inventions.

Turning first to FIG. 1, an exemplary SCM system 10 generally includes a plurality of implantable neuromodulation leads 12, an implantable pulse generator (IPG) 14, an external remote controller RC 16, a clinician's programmer (CP) 18, an external trial modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one. Alternatively, a surgical paddle lead in can be used in place of one or more of the percutaneous leads. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation energy delivered to the patient. Thus, any functions described herein with respect to the IPG 14 can likewise be performed with respect to the ETM 20.

The RC 16 may be used to telemetrically control the ETM 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. The CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18). In the present invention, the CP 18 may be used to select electrodes most suitable for sub-threshold modulation therapy, as will be described in further detail below.

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, ETM 20, and external charger 22 will not be described herein. Details of exemplary embodiments of these devices are disclosed in U.S. Pat. No. 6,895,280, which is expressly incorporated herein by reference.

Figure 2:
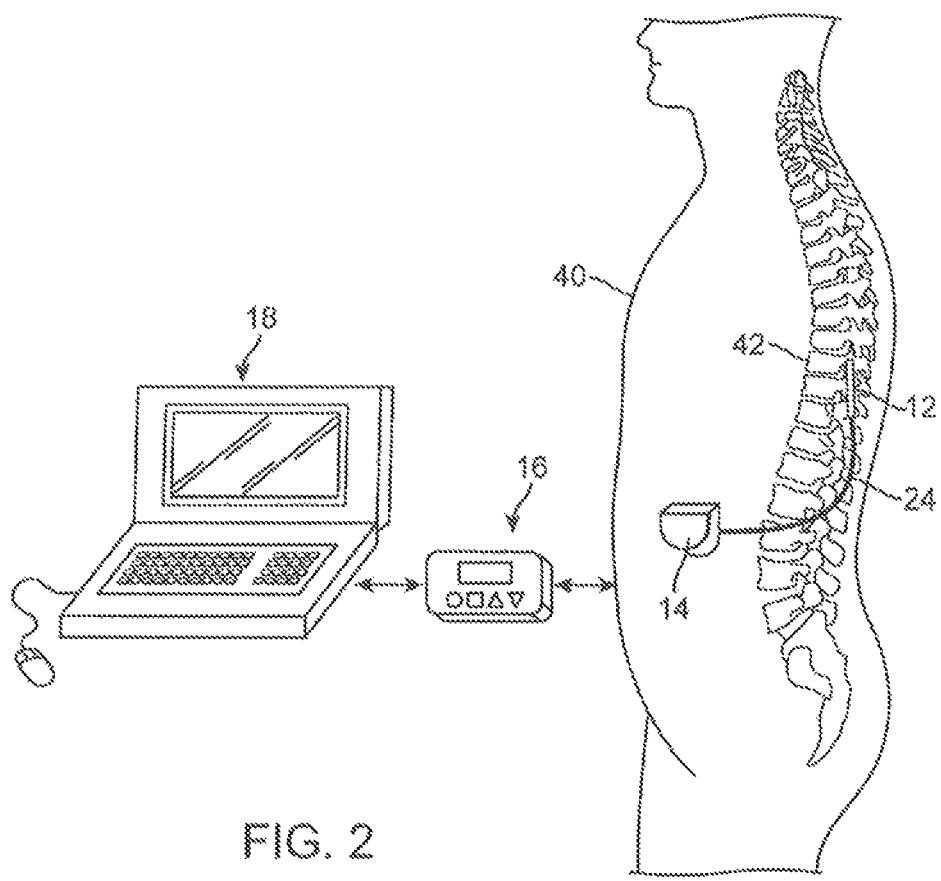
FIG. 2 is a plan view of the SCM system of FIG. 1 in use with a patient.

As shown in FIG. 2, the neuromodulation leads 12 are implanted within the spinal column 42 of a patient 40. The preferred placement of the neuromodulation leads 12 is adjacent, i.e., resting upon, the spinal cord area to be stimulated. Due to the lack of space near the location where the neuromodulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neuromodulation leads 12. As there shown, the CP 18 communicates with the IPG 14 via the RC 16.

More significant to the present inventions, the CP 18 is configured for automatically selecting, or aiding the user in selecting, one or more effective electrodes for delivering sub-threshold modulation therapy to the patient. To this end, as will be described in further detail below, the CP 18 uses a combination of a ratio between an anodic perception threshold and a cathodic perception threshold for each and an anodic paresthesia map for each of the electrodes 26 in automatically selecting or providing suggestions to the user for selecting the effective electrode(s) for sub-threshold modulation therapy.

Figure 3:
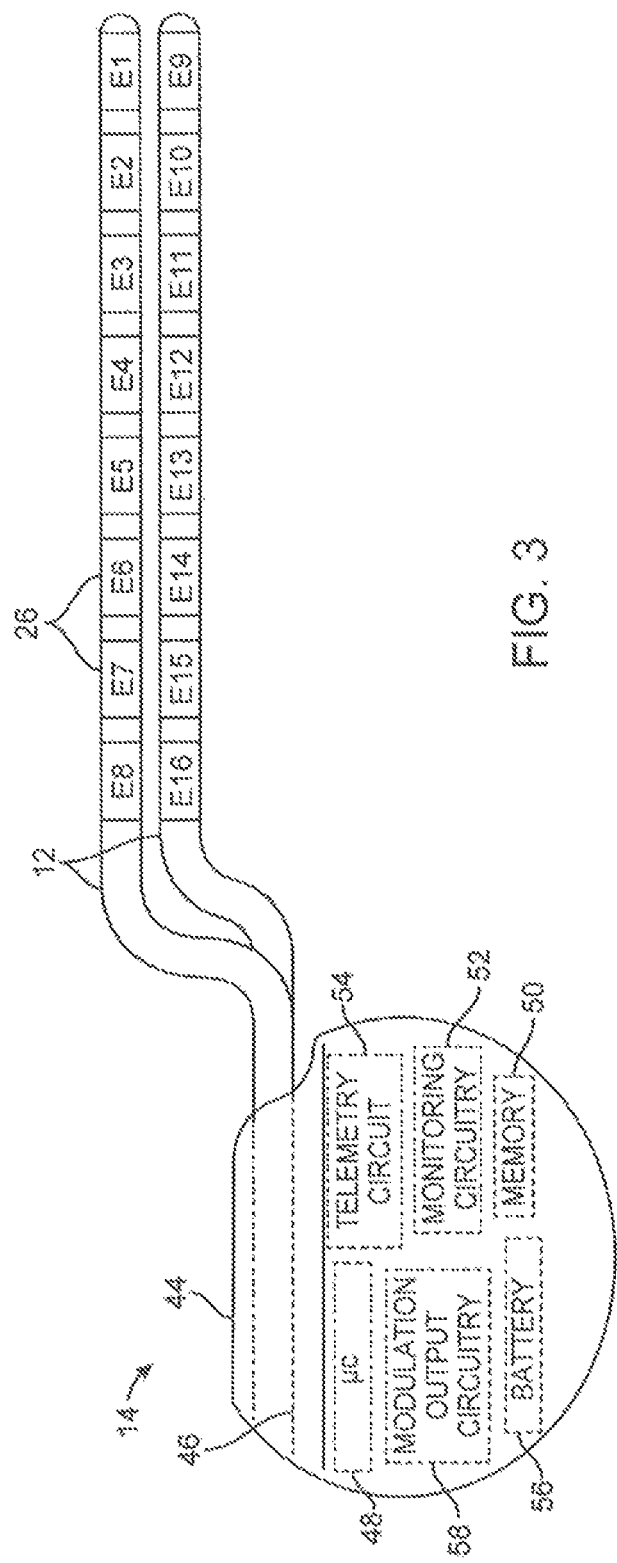
FIG. 3 is a plan view of an implantable pulse generator (IPG) and two percutaneous leads used in the SCM system of FIG. 1.

Referring now to FIG. 3, the external features of the neuromodulation leads 12 and the IPG 14 will be briefly described. One of the neuromodulation leads 12a has eight electrodes 26 (labeled E1-E8), and the other neuromodulation lead 12b has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neuromodulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

The IPG 14 comprises electronic components, such as a controller/processor (e.g., a microcontroller) 48, memory 50, monitoring circuitry 52, telemetry circuitry 54, a battery 56, modulation output circuitry 58, and other suitable components known to those skilled in the art. The microcontroller 48 executes a suitable program stored in memory 50, for directing and controlling the neuromodulation performed by 14.

The monitoring circuitry 52 is configured for monitoring the status of various nodes or other points throughout the IPG 14, e.g., power supply voltages, temperature, battery voltage, and the like. The monitoring circuitry 52 may also be configured for sensing evoked compound action potentials (eCAPs) in response to the delivery of super-threshold electrical energy. As will be described in further detail below, the CP 18 may utilize these sensed eCAPs to determine perception thresholds of the patient.

Telemetry circuitry 54, including an antenna (not shown), is configured for receiving programming data (e.g., the operating program and/or modulation parameters) from the RC 16 and/or CP 18 in an appropriate modulated carrier signal, which the programming data is then stored in the memory (not shown). The telemetry circuitry 54 is also configured for transmitting status data to the RC 16 and/or CP 18 (including the sensed eCAPs) in an appropriate modulated carrier signal. The battery 56, which may be a rechargeable lithium-ion or lithium-ion polymer battery, provides operating power to IPG 14. The monitoring circuitry 52 is configured for monitoring the present capacity level of the battery 56.

The modulation output circuitry 58 is configured for, under control of the microcontroller 48, independently generating both super-threshold modulation electrical energy and sub-threshold electrical energy to each of the electrodes 26. In the illustrated embodiment, microcontroller 48 can individually control the magnitude of electrical current flowing through each of the electrodes 26. In this case, it is preferred that the modulation output circuitry 58 have independent current sources (not shown) for selectively generating individual current-regulated amplitudes for each electrode. Although this system is optimal to take advantage of the invention, the modulation output circuitry 58 may have independent voltage sources. While individually programmable electrode amplitudes are optimal to achieve fine control, a single output source switched across electrodes may also be used, although with less fine control in programming. Mixed current and voltage regulated devices may also be used in the modulation output circuitry 58.

In the illustrated embodiment, the modulation output circuitry 58 delivers electrical pulse trains to the electrodes 26 in accordance with a set of modulation parameters. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the modulation on duration X and modulation off duration Y).

Electrical modulation will occur between two (or more) activated electrodes, one of which may be the IPG case 44. Modulation energy may be transmitted to the tissue in a monopolar or multipolar (e.g., bipolar, tripolar, etc.) fashion. Monopolar modulation occurs when a selected one of the lead electrodes 26 is activated along with the case of the IPG 14, so that modulation energy is transmitted between the selected electrode 26 and case. Bipolar modulation occurs when two of the lead electrodes 26 are activated as anode and cathode, so that modulation energy is transmitted between the selected electrodes 26. For example, electrode E3 on the first lead 12*a* may be activated as an anode at the same time that electrode E11 on the second lead 12*b* is activated as a cathode. Tripolar modulation occurs when three of the lead electrodes 26 are activated, two as anodes and the remaining one as a cathode, or two as cathodes and the remaining one as an anode. For example, electrodes E4 and E5 on the first lead 12*a* may be activated as anodes at the same time that electrode E12 on the second lead 12*b* is activated as a cathode.

Any of the electrodes E1-E16 and case electrode may be assigned to up to k possible groups or timing "channels." in one embodiment, k may equal four. The timing channel identifies which electrodes are selected to synchronously source or sink current to create an electric field in the tissue to be modulated. Amplitudes and polarities of electrodes on a channel may vary. In particular, the electrodes can be selected to be positive (sourcing current), negative (sinking current), or off (no current) polarity in any of the k timing channels.

Figure 4:
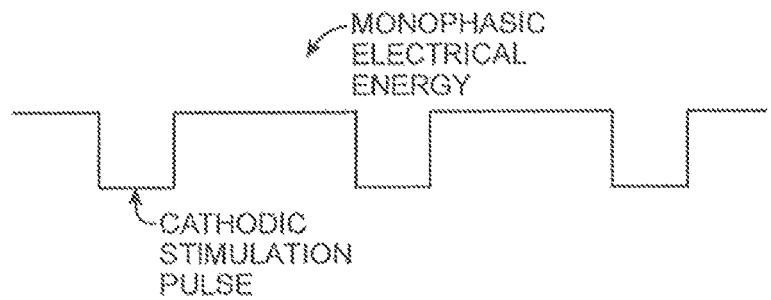
FIG. 4 is a plot of monophasic cathodic electrical modulation energy.

The modulation energy may be delivered between a specified group of electrodes as monophasic electrical energy or multiphasic electrical energy. As illustrated in FIG. 4, monophasic electrical energy takes the form of an electrical pulse train that includes either all negative pulses (cathodic), or alternatively all positive pulses (anodic).

Figure 5A:
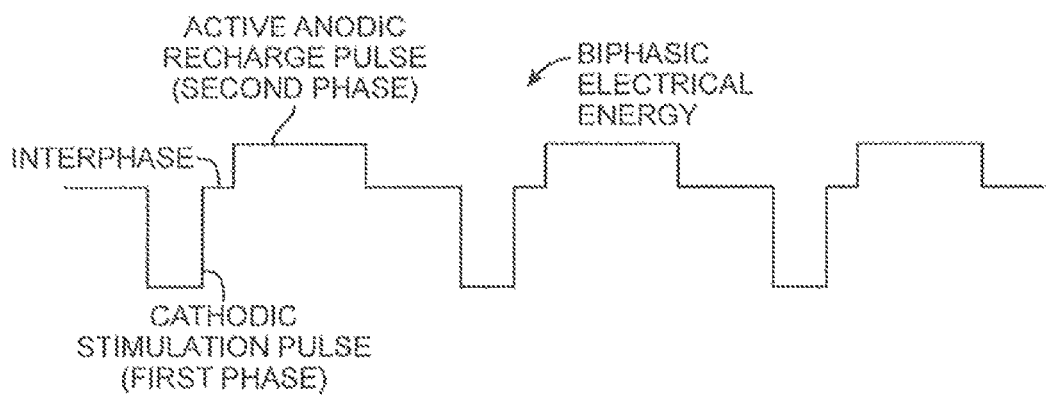
FIG. 5a is a plot of biphasic electrical modulation energy having a cathodic modulation pulse and an active charge recovery pulse.
Figure 5B:
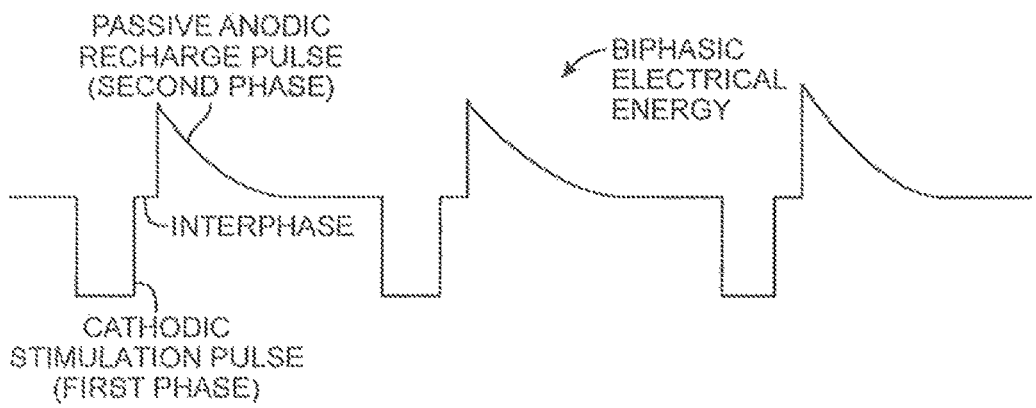
FIG. 5b is a plot of biphasic electrical modulation energy having a cathodic modulation pulse and a passive charge recovery pulse.

Multiphasic electrical energy includes a series of pulses that alternate between positive and negative. For example, as illustrated in FIGS. 5*a* and 5*b*, multiphasic electrical energy may include a series of biphasic pulses, with each biphasic pulse including a cathodic (negative) modulation phase and an anodic (positive) charge recovery pulse phase that is generated after the modulation phase to prevent direct current charge transfer through the tissue, thereby avoiding electrode degradation and cell trauma. That is, charge is conveyed through the electrode-tissue interface via current at an electrode during a modulation period (the length of the modulation phase), and then pulled back off the electrode-tissue interface via an oppositely polarized current at the same electrode during a recharge period (the length of the charge recovery phase).

The second phase may be an active charge recovery phase (FIG. 5*a*), wherein electrical current is actively conveyed through the electrode via current or voltage sources, or the second phase may be a passive charge recovery phase (FIG. 5*b*), wherein electrical current is passively conveyed through the electrode via redistribution of the charge flowing from coupling capacitances present in the circuit. Using active recharge, as opposed to passive recharge, allows faster recharge, while avoiding the charge imbalance that could otherwise occur. Another electrical pulse parameter in the form of an interphase can define the time period between the pulses of the biphasic pulse (measured in microseconds). Although the modulation and charge recovery phases of the biphasic pulses illustrated in FIGS. 5*a* and 5*b* are cathodic and anodic, respectively, it should be appreciated that the modulation and charge recovery pulses of biphasic pulses may be anodic and cathodic respectively, depending upon the desired therapeutic result.

Further details discussing the detailed structure and function of IPGs are described more fully in U.S. Pat. Nos. 6,516,227 and 6,993,384, which are expressly incorporated herein by reference.

It should be noted that rather than an IPG, the SCM system 10 may alternatively utilize an implantable receiver-modulator (not shown) connected to the neuromodulation leads 12. In this case, the power source, e.g., a battery, for powering the implanted receiver, as well as control circuitry to command the receiver-modulator, will be contained in an external controller inductively coupled to the receiver-modulator via an electromagnetic link. Data/power signals are transcutaneously coupled from a cable-connected transmission coil placed over the implanted receiver-modulator. The implanted receiver-modulator receives the signal and generates the modulation in accordance with the control signals.

As briefly discussed above, the CP 18 greatly simplifies the programming of multiple electrode configurations, allowing the user (e.g., the physician or clinician) to readily determine the desired modulation parameters to be programmed into the IPG 14, as well as the RC 16. Thus, modification of the modulation parameters in the programmable memory of the IPG 14 after implantation is performed by the user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using m ware or hardware. In any event, the CP 18 may actively control the characteristics of the electrical stimulation generated by the IPG 14 to allow the optimum modulation parameters to be determined based on patient feedback and for subsequently programming the IPG 14 with the optimum modulation parameter.

To allow the user to perform these functions, the CP 18 includes a user input device (e.g., a mouse 72 and a keyboard 74), and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74.

In the illustrated embodiment described below, the display screen 76 takes the form of a conventional screen, in which case, a virtual pointing device, such as a cursor controlled by a mouse, joy stick, trackball, etc., can be used to manipulate graphical objects on the display screen 76. In alternative embodiments, the display screen 76 takes the form of a digitizer touch screen, which may either passive or active. If passive, the display screen 76 includes detection circuitry (not shown) that recognizes pressure or a change in an electrical current when a passive device, such as a finger or non-electronic stylus, contacts the screen. If active, the display screen 76 includes detection circuitry (not shown) that recognizes a signal transmitted by an electronic pen or stylus. In either case, detection circuitry is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. When the pointing device touches or otherwise is in close proximity to the screen, the graphical object on the screen adjacent to the touch point is "locked" for manipulation, and when the pointing device is moved away from the screen the previously locked object is unlocked. Further details discussing the use of a digitizer screen for programming are set forth in U.S. Provisional Patent Application Ser. No. 61/561,760, entitled "Technique for Linking Electrodes Together during Programming of Neurostimulation System," which is expressly incorporated herein by reference.

Figure 6:
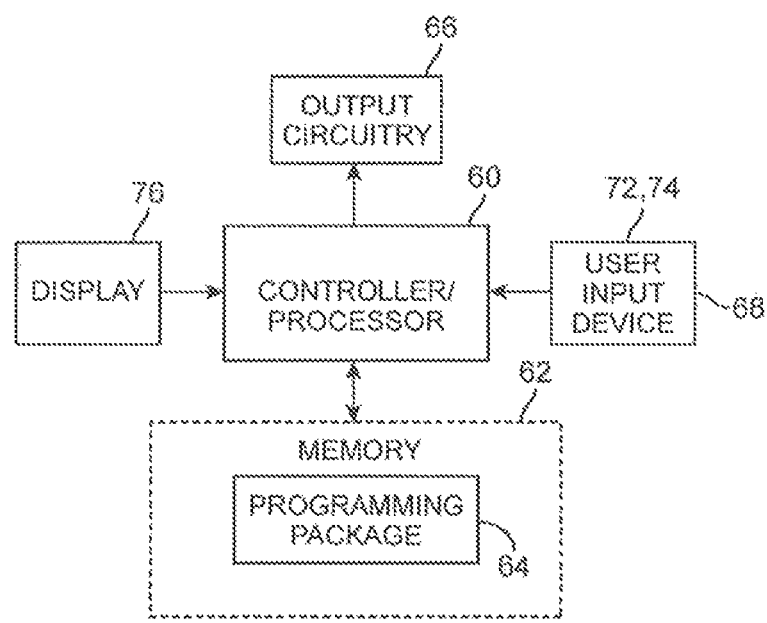
FIG. 6 is a block diagram of a clinician's programmer (CP) used in the SCM system of FIG. 1.

Referring now to FIG. 6, the CP 18 includes a controller/processor 60 (e.g., a central processor unit (CPU)) and memory 62 that stores a programming package 64, which can be executed by the controller/processor 60 to allow the user to program the IPG 14 and RC 16. In addition, the CP 18 further includes a user input device 68 (such as the mouse 72 or the keyboard 74 described above) to provide user commands. Notably, while the controller/processor 60 is shown in FIG. 6 as a single device, the processing functions and controlling functions can be performed by a separate controller and processor. Thus, it can be appreciated that the controlling functions described below as being performed by the CP 18 can be performed by a controller, and the processing functions described below as being performed by the CP 18 can be performed by the processor of the RC 16.

Execution of the programming package 64 by the controller/processor 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads 12, and select and program the IPG 14 with modulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Modulation energy Among Multiple Neuromodulation Electrodes," which are expressly incorporated herein by reference. Execution of the programming package 64 provides a user interface that conveniently allows a user to program the IPG 14.

Figure 7:
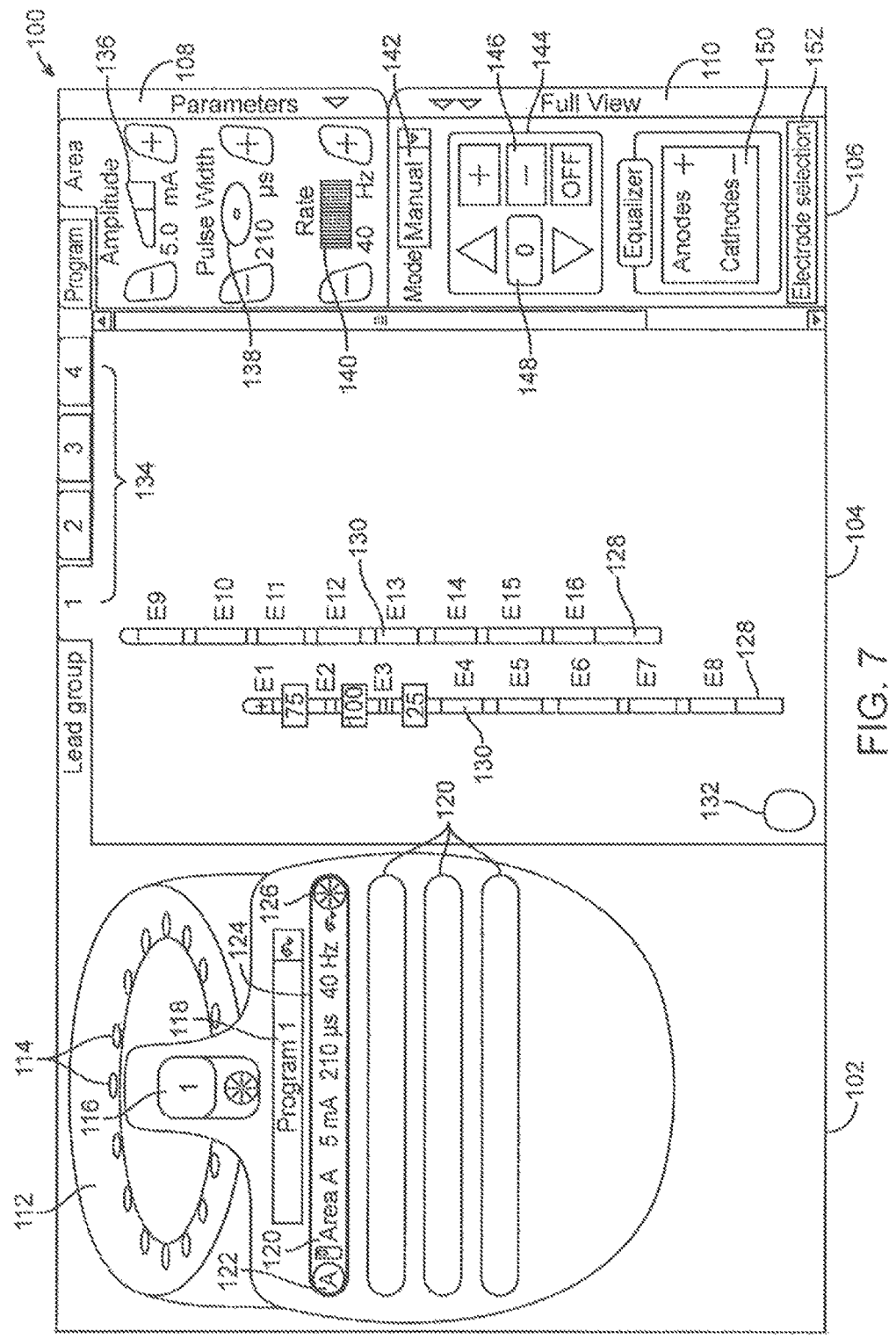
FIG. 7 is a plan view of a user interface of the CP of FIG. 6 for programming the IPG of FIG. 3 in a manual programming mode.

Referring now to FIG. 7, a programming screen 100 that can be generated by the CP 18 to allow a user to program the IPG 14 will be described. In the illustrated embodiment, the programming screen 100 comprises three panels: a program selection panel 102, a lead display panel 104, and a modulation parameter adjustment panel 106. Some embodiments of the programming screen 100 may allow for closing and expanding one or both of the lead display panel 102 and the parameter adjustment panel 106 by clicking on the tab 108 (to show or hide the parameter adjustment panel 106) or the tab 110 (to show or hide the full view of both the lead selection panel 104 and the parameter adjustment panel 106).

The program selection panel 102 provides information about modulation programs and coverage areas that have been, or may be, defined for the IPG 14. In particular, the program selection panel 102 includes a carousel 112 on which a plurality of modulation programs 114 (in this case, up to sixteen) may be displayed and selected. The program selection panel 102 further includes a selected program status field 116 indicating the number of the modulation program 114 that is currently selected (any number from "1" to "16"). In the illustrated embodiment, program 1 is the only one currently selected, as indicated by the number "1" in the field 116. The program selection panel 102 further comprises a name field 118 in which a user may associate a unique name to the currently selected modulation program 114.

The program selection panel 102 further comprises a plurality of coverage areas 120 (in this case, up to four) with which a plurality of modulation parameter sets can respectively be associated to create the currently selected modulation program 114 (in this case, program 1). Each coverage area 120 that has been defined includes a designation field 122 (one of letters "A"-"D"), and an electrical pulse parameter field 124 displaying the electrical pulse parameters, and specifically, the pulse amplitude, pulse width, and pulse rate, of the modulation parameter set associated with the that coverage area. In this example, only coverage area A is defined for program 1, as indicated by the "A" in the designation field 122. The electrical pulse parameter field 124 indicates that a pulse amplitude of 5 mA, a pulse width of 210 μs, and a pulse rate of 40 Hz has been associated with coverage area A.

Each of the defined coverage areas 120 also includes a selection icon 126 that can be alternately actuated to activate or deactivate the respective coverage area 120. When a coverage area is activated, an electrical pulse train is delivered from the IPG 14 to the electrode array 26 in accordance with the modulation parameter set associated with that coverage area. Notably, multiple ones of the coverage areas 120 can be simultaneously activated by actuating the selection icons 126 for the respective coverage areas. In this case, multiple electrical pulse trains are concurrently delivered from the IPG 14 to the electrode array 26 during timing channels in an interleaved fashion in accordance with the respective modulation parameter sets associated with the coverage areas 120. Thus, each coverage area 120 corresponds to a timing channel.

To the extent that any of the coverage areas 120 have not been defined (in this case, three have not been defined), they include text "click to add another program area"), indicating that any of these remaining coverage areas 120 can be selected for association with a modulation parameter set. Once selected, the coverage area 120 will be populated with the designation field 122, electrical pulse parameter field 124, and selection icon 126.

The lead display panel 104 includes graphical leads 128, which are illustrated with eight graphical electrodes 130 each (labeled electrodes E1-E8 for the first lead 128 and electrodes E9-E16 for second lead 128). The lead display panel 104 also includes a graphical case 132 representing the case 44 of the IPG 14. The lead display panel 104 further includes lead group selection tabs 134 (in this case, four), any of which can be actuated to select one of four groups of graphical leads 128. In this case, the first lead group selection tab 134 has been actuated, thereby displaying the two graphical leads 128 in their defined orientation. In the case where additional leads 12 are implanted within the patient, they can be associated with additional lead groups.

The parameter adjustment panel 106 also includes a pulse amplitude adjustment control 136 (expressed in milliamperes (mA)), a pulse width adjustment control 138 (expressed in microseconds (μs)), and a pulse rate adjustment control 140 (expressed in Hertz (Hz)), which are displayed and actuatable in all the programming modes. Each of the controls 136-140 includes a first arrow that can be actuated to decrease the value of the respective modulation parameter and a second arrow that can be actuated to increase the value of the respective modulation parameter. Each of the controls 136-140 also includes a display area for displaying the currently selected parameter. In response to the adjustment of any of electrical pulse parameters via manipulation of the graphical controls in the parameter adjustment panel 106, the controller/processor 80 generates a corresponding modulation parameter set (with a new pulse amplitude, new pulse width, or new pulse rate) and transmits it to the IPG 14 via the telemetry circuitry 86 for use in delivering the modulation energy to the electrodes 26.

The parameter adjustment panel 106 includes a pull-down programming mode field 142 that allows the user to switch between a manual programming mode a navigation programming mode, and a sub-threshold programming mode. Each of these programming modes allows a user to define a modulation parameter set for the currently selected coverage area 120 of the currently selected program 114 via manipulation of graphical controls in the parameter adjustment panel 106 described above, as well as the various graphical controls described below.

The manual programming mode is designed to allow the user to manually define the fractionalized electrical current for the electrode array with maximum flexibility, whereas the electronic trolling programming mode is designed to quickly sweep the electrode array using a limited number of electrode configurations to gradually steer an electrical field relative to the modulation leads until the targeted modulation site is located, whereas the navigation programming mode is designed to sweep the electrode array using a wide number of electrode configurations to shape the electrical field, thereby fine tuning and optimization the modulation coverage for patient comfort. Further programming modes, such as exploration programming mode and sub-threshold programming mode are described in U.S. Provisional Patent Application Ser. No. 61/801,917, entitled "Systems and Methods for Delivering Sub-Threshold Therapy to a Patient," which is expressly incorporated herein by reference.

As shown in FIG. 6, the manual programming mode has been selected. In the manual programming mode, each of the electrodes 130 of the graphical leads 128, as well as the graphical case 132, may be individually selected, allowing the clinician to set the polarity (cathode or anode) and the magnitude of the current (percentage) allocated to that electrode 130, 132 using graphical controls located in an amplitude/polarity area 144 of the parameter adjustment panel 106.

In particular, a graphical polarity control 146 located in the amplitude/polarity area 144 includes a "+" icon, a "−"

icon, and an "OFF" icon, which can be respectively actuated to toggle the selected electrode 130, 132 between a positive polarization (anode), a negative polarization (cathode), and an off-state. An amplitude control 148 in the amplitude/polarity area 144 includes an arrow that can be actuated to decrease the magnitude of the fractionalized current of the selected electrode 130, 132, and an arrow that can be actuated to increase the magnitude of the fractionalized current of the selected electrode 130, 132. The amplitude control 148 also includes a display area that indicates the adjusted magnitude of the fractionalized current for the selected electrode 134. The amplitude control 148 is preferably disabled if no electrode is visible and selected in the lead display panel 104. In response to the adjustment of fractionalized electrode combination via manipulation of the graphical controls in the amplitude/polarity area 144, the controller/processor 80 generates a corresponding modulation parameter set (with a new fractionalized electrode combination) and transmits it to the IPG 14 via the telemetry circuitry 86 for use in delivering the modulation energy to the electrodes 26.

In the illustrated embodiment, electrode E2 has been selected as a cathode to which 100% of the cathodic current has been allocated, and electrodes E1 and E3 have been respectively selected as anodes to which 25% and 75% of the anodic current has been respectively allocated. Electrode E15 is shown as being selected to allow the user to subsequently allocate the polarity and fractionalized electrical current to it via the graphical controls located in the amplitude/polarity area 144. Although the graphical controls located in the amplitude/polarity area 144 can be manipulated for any of the electrodes, a dedicated graphical control for selecting the polarity and fractionalized current value can be associated with each of the electrodes, as described in U.S. Patent Publication No. 2012/0290041, entitled "Neurostimulation System with On-Effector Programmer Control," which is expressly incorporated herein by reference.

The parameter adjustment panel 106, when the manual programming mode is selected, also includes an equalization control 150 that can be actuated to automatically equalize current allocation to all electrodes of a polarity selected by respective "Anode +" and "Cathode −" icons. Unlike the other programming modes described in further detail below, the ranges of pulse rates and pulse widths of the modulation parameter sets defined during the manual programming mode are not limited to those known to result in only one of super-threshold therapy and sub-threshold therapy. For example, the lower limit of the pulse amplitude may be as low as 0.1 mA, wherein as the upper limit of the pulse amplitude may be as high as 20 mA. The lower limit of the pulse width may be as low as 2 μs, whereas the upper limit of the pulse width may be as high as 1000 μs. For example, the lower limit of the pulse rate may be as low as 1 Hz, whereas the upper limit of the pulse rate may be as high as 50 KHz. In the illustrated embodiment, a pulse amplitude of 5 mA, a pulse width of 210 μs, and a pulse rate of 40 Hz have been selected. Thus, during the manual programming mode, the selected coverage area 120 of the selected program 114 can be programmed with a modulation parameter set designed to either deliver super-threshold therapy or sub-threshold therapy to the patient.

Figure 8:
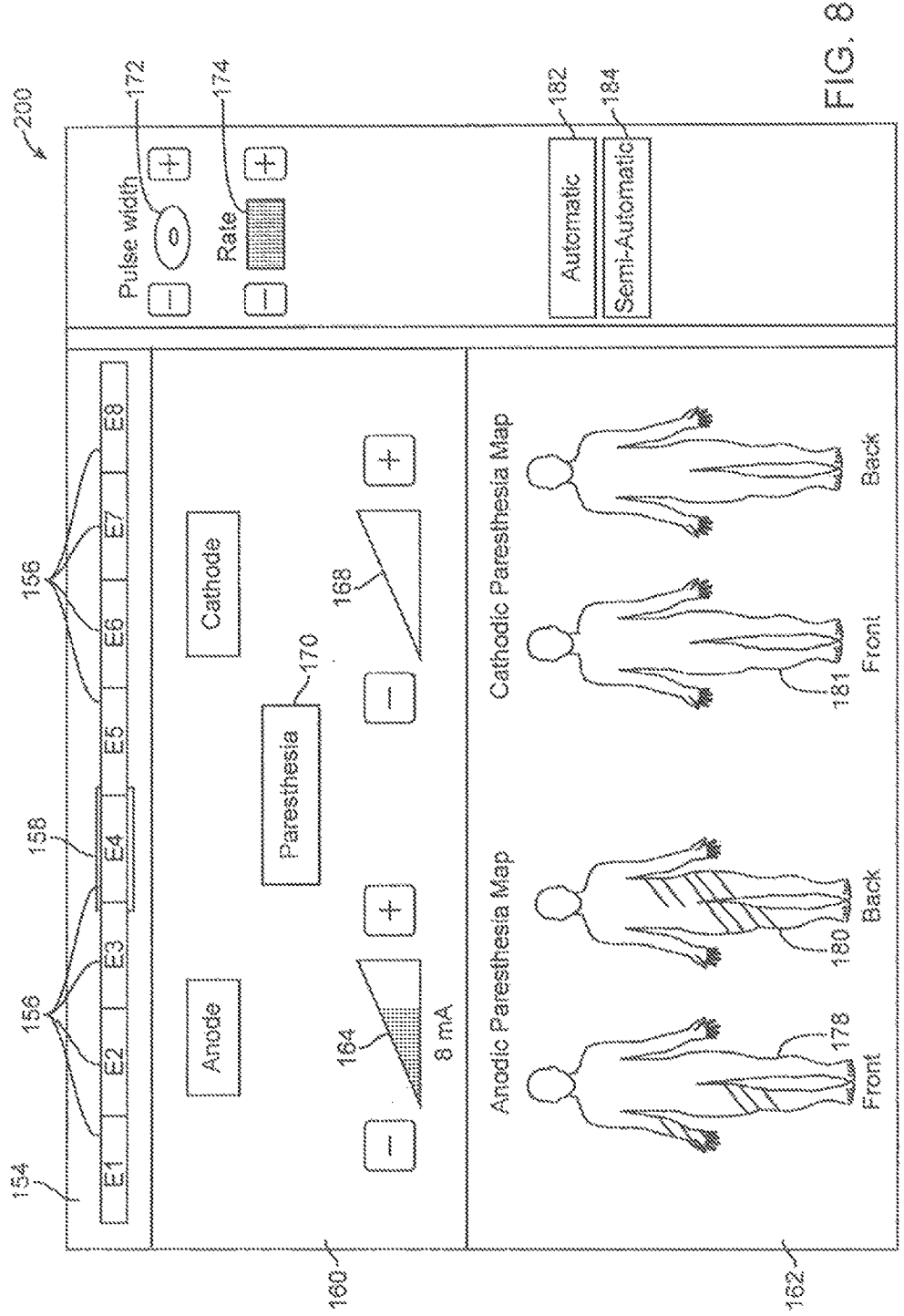
FIG. 8 is a plan view of a user interface of the CP of FIG. 6 for determining perception thresholds and creating paresthesia maps.

More significant to the present inventions, when in the manual programming mode, the parameter adjustment panel 106 also includes an electrode-selection control 152 that can be actuated to cause the CP 18 to generate an electrode selection screen 200, as illustrated in FIG. 8. In the electrode-selection screen 200, one or more effective electrodes can be selected from the electrodes 26 to deliver sub-threshold modulation therapy to the patient. The effective electrode(s) are selected based on a combination of a ratio between an anodic perception threshold and a cathodic perception threshold and the anodic paresthesia coverage for each of the electrodes. The electrode selection screen 200 allows the user to enter in relevant information related to selecting effective electrode(s) from the electrodes 26.

To this end, the electrode selection screen 200 includes an electrode panel 154 comprising an electrode selection control 156 for all the electrodes 26. The electrode selection control 156 may include a slider (or any other selection tool) that can be actuated to select a particular electrode. In an alternate embodiment, the electrode panel 154 may include an entry box to type the number of one of the electrodes 26. In another alternative embodiment, the electrode panel may include a list of electrodes represented by graphical elements any of which might be actuated to select the particular electrode. In the illustrated embodiment, the electrode selection control 156 includes all the electrodes 130 of graphical lead 128 out of which electrode E4 has been actuated. Although the illustrated embodiment depicts electrodes E1-E8 of only one neuromodulation lead 12, it should be appreciated that the electrode panel 154 may include an electrode selection control 156 for the electrodes 26 of all the neuromodulation leads 12 implanted in the patient (in the illustrated case, electrodes E1-E16 for two neurostimulation leads 12).

When an electrode is selected using the electrode selection control 156, a perception threshold panel 160 and a paresthesia map 162 for that electrode is automatically displayed. The perception threshold panel 160 is used to determine and record both the anodic and cathodic perception thresholds of super-threshold electrical energy for the selected electrode. The perception threshold panel 160 also includes amplitude adjustment controls 164 and 168 (expressed in milliamperes (mA)), to be used when determining the anodic perception threshold and the cathodic perception threshold respectively. The electrode selection screen 200 also includes a pulse width adjustment control 172 and a pulse rate adjustment control 174 to enable the user to respectively control the pulse width and pulse rate of super-threshold electrical energy delivered from the electrodes 26. Super-threshold pulse trains are typically delivered at a relatively high pulse amplitude (e.g., 5 ma), a relatively low pulse rate (e.g., less than 1500 Hz, preferably less than 500 Hz), and a relatively high pulse width (e.g., greater than 100 μs, preferably greater than 200 μs).

The amplitude adjustment controls 164 and 168 are displayed and actuatable for each electrode. Each of the controls for 164, 168, 172 and 174 includes a first arrow that can be actuated to decrease the value of the parameter and a second arrow that can be actuated to increase the parameter. The controls 164, 168, 172 and 174 also include a display area for displaying the currently selected parameter. In response to the adjustment of any of electrical pulse parameters via manipulation of the graphical controls, the controller 60 generates a corresponding modulation parameter set (with a new pulse amplitude, new pulse width, or new pulse rate) and transmits it to the IPG 14 via the telemetry circuitry 54 for use in delivering the modulation energy to the electrodes 26.

To determine the anodic perception threshold, the user may first configure the selected electrode as an anode, and incrementally increase the amplitude of the super-threshold electrical energy delivered from the electrode using the amplitude adjustment control 164. Similarly, to determine the cathodic perception threshold of the selected electrode, the user may configure the electrode as a cathode and incrementally increase the amplitude of the super-threshold electrical energy delivered from the electrode using amplitude adjustment control 168. It should be appreciated that the anodic perception threshold and the cathodic perception threshold are determined separately, such that when the amplitude adjustment control 164 is actuated, the amplitude of cathodic energy is immediately set to 0 on the amplitude adjustment control 168, and when the amplitude adjustment control 168 is actuated, the amplitude of the anodic energy is immediately set to 0 on the amplitude adjustment control 164.

The perception threshold panel 160 includes a paresthesia recording button 170 that may be actuated when the patient reports experiences a feeling of paresthesia in response to either the anodic super-threshold electrical energy being delivered from the selected electrode or the cathodic super-threshold electrical energy being delivered from the selected electrode. When the paresthesia recording button 170 is selected, the present amplitude of the anodic electrical energy, as set by the amplitude adjustment control 164, is recorded as the anodic perception threshold in the memory 62, or the present amplitude of the cathodic electrical energy, as set by the amplitude adjustment control 168, is recorded as the cathodic perception threshold in the memory 62. In alternative embodiments, the perception threshold panel 160 may graphically display the recorded anodic and cathodic perception thresholds.

In an alternate embodiment, the anodic perception threshold and/or the cathodic perception threshold may be automatically determined and stored by sensing evoked compound action potentials (eCAPs) in response to the delivery of super-threshold anodic electrical energy and super-threshold cathodic electrical energy from each of the electrodes 26. ECAPs may be measured by generating an electrical field which is strong enough to depolarize neurons adjacent to the stimulated electrode beyond a threshold level, thereby inducing the firing of action potentials that propagate along the neuronal fibers.

Characteristics of eCAPs that correlate to anodic perception thresholds and cathodic perception thresholds may be stored as a template for matching against the actual eCAPs. Thus, when the user incrementally increases the amplitude of the super-threshold electrical energy delivered from the electrode using amplitude adjustment controls 164 and 168, the monitoring circuitry 56 of the IPG 14 senses the eCAPs and communicates them to control circuitry. When the measured eCAP matches the template eCAP, the amplitude of the electrical energy that caused the measured eCAP is automatically determined as either the anodic perception threshold or the cathodic perception threshold for that electrode based on whether the electrode was configured as an anode or a cathode. Further details on eCAPs are disclosed in U.S. Provisional Patent Application Ser. No. 61/768,295, entitled "Neurostimulation system and method for automatically adjusting stimulation and reducing energy requirements using evoked action potential," which is expressly incorporated herein by reference. The paresthesia map 162 depicts regions of paresthesia perceived by the patient in response to both anodic and cathodic delivery of super-threshold electrical energy. In response to input from the patient, a region or regions of paresthesia may be actuated on a mock body figure to highlight an estimated region (or regions) of perceived paresthesia. The highlighted sections of the mock body figure are recorded as the anodic paresthesia map or the cathodic paresthesia map in the memory 62.

In the illustrated embodiment, regions of paresthesia for anodic super-threshold electrical energy delivered through electrode E4 have already been selected for an anodic paresthesia map as signified by the highlighted sections of a "Front" mock body FIG. 178 and a "Back" mock body FIG. 180.

Although paresthesia maps may be created for perceived paresthesia resulting from the delivery of super-threshold anodic electrical energy and the delivery of super-threshold cathodic electrical energy, it has been shown that paresthesia observed during super-threshold anodic stimulation is a better predictor for effective sub-threshold therapy. Therefore, the description of this embodiment will focus on anodic paresthesia maps, although both anodic and cathodic paresthesia maps may be generated.

By separately selecting each electrode using the electrode selection control 156, a perception threshold panel 160 and a paresthesia map 162 for the respectively selected electrode is displayed on the electrode selection screen 200, thereby allowing the user to determine and record both the anodic and cathodic perception thresholds and create paresthesia maps for each of the electrodes 26. Perception thresholds and paresthesia maps may be created for all the electrodes 26 or only some of the electrodes 26 based on user discretion.

In addition to allowing the user to determine the anodic and cathodic perception thresholds and paresthesia coverage for each of the electrodes 26, the electrode selection screen 200 enables the user to select whether the CP 18 selects the effective electrode(s) without further user input or selects the effective electrode(s) in conjunction with further user input. In particular, the electrode selection screen 200 includes both an "Automatic" button 182 and a "Semi-Automatic" button 184, which when actuated, respectively place the CP 18 in either an automatic electrode selection mode or a semi-automatic electrode selection mode. In the automatic mode, an effective electrode is automatically selected without any user input. In the semi-automatic mode, the effective electrodes are selected with input from the user. Although the illustrated embodiment depicts both the automatic and semi-automatic modes of electrode selection, it should be appreciated that versions of the CP 18 may be programmed to contain only one of the two modes.

In the automatic mode, the controller 60 automatically selects the effective electrode by computing a total score for each electrode based on a threshold score related to a ratio between the anodic perception threshold and the cathodic perception threshold and a coverage score related to match between the anodic paresthesia map for the electrode and a predetermined pain map for the patient.

Figure 9:
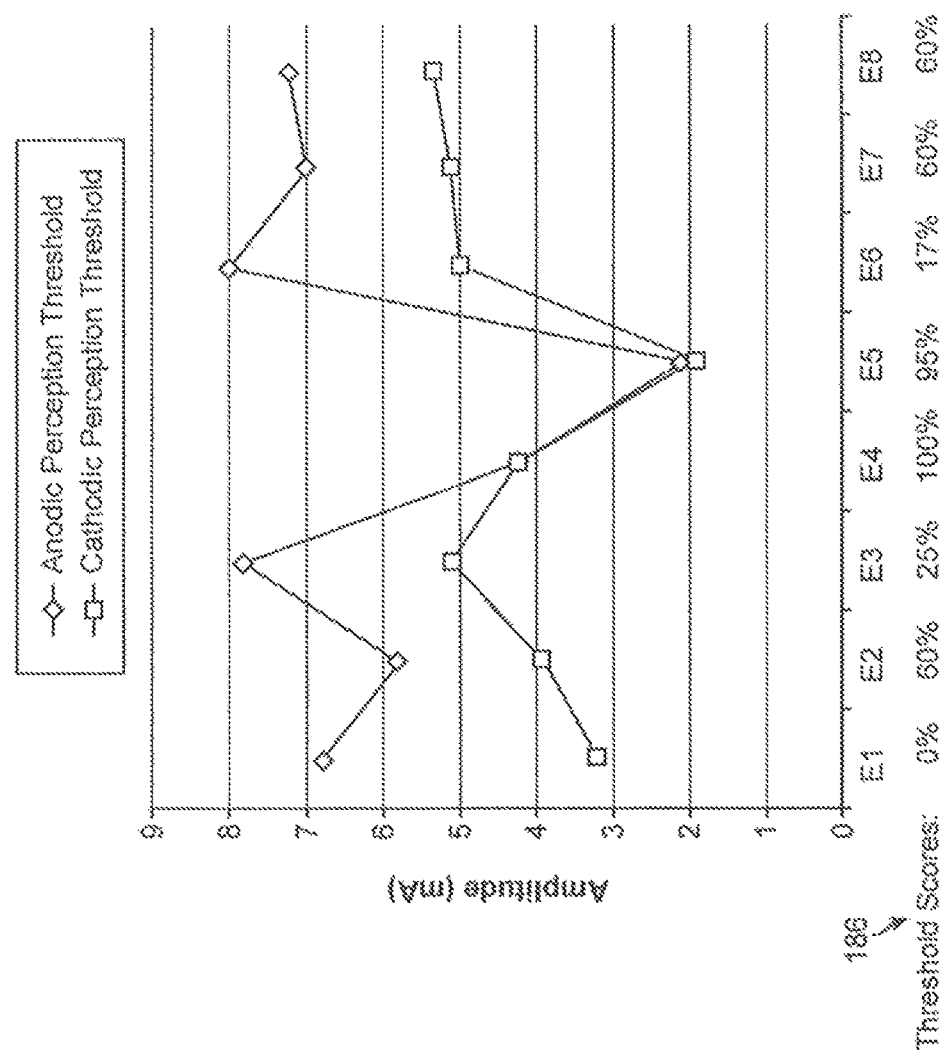
FIG. 9 is a plot of anodic perception thresholds and cathodic perception thresholds of the electrodes recorded in the CP of FIG. 1.

To determine a threshold score for the electrode, the controller 60 automatically computes a ratio between the anodic perception threshold and the cathodic perception threshold for each electrode. It has been observed in empirical studies that electrodes having ratios between the anodic perception threshold and the cathodic perception threshold closest to unity are the most effective for delivering sub-threshold modulation energy. As shown in FIG. 9, threshold scores 186 for the electrodes 26 (E1-E8 in the illustrated embodiment) may be calculated based on a percentage proximity of the ratios to unity. For example, when the anodic perception threshold and the cathodic perception threshold are identical, the threshold score may be 100, as is the case for electrode E4 in the illustrated embodiment. Similarly, the electrode having the largest difference between the anodic perception threshold and the cathodic perception threshold may be set as 0, as is the case for electrode E1 in the illustrated embodiment. The rest of the threshold scores 186 may be calculated within the range of ratios between 0 and 100 to generate threshold scores for all the electrodes 26. It should be appreciated that the illustrated embodiment represents only one method of calculating the threshold scores 186, and any other suitable algorithm or calculation may be similarly used.

Figure 10:
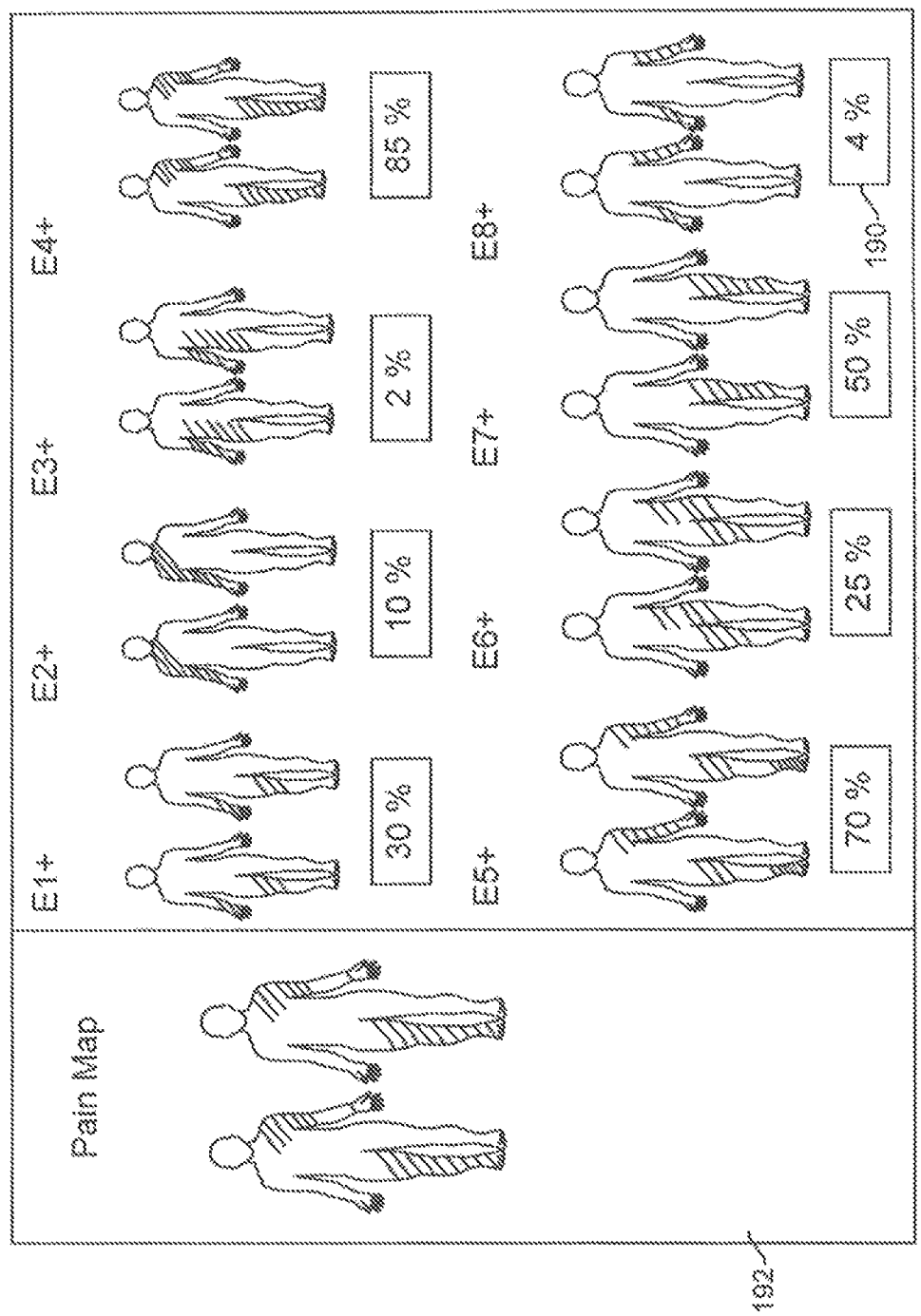
FIG. 10 is a plan view of anodic paresthesia maps for the electrodes of FIG. 1 and a predetermined pain map.

The controller 60 also computes a coverage score for each of the electrodes 26 based on a relative match between each body region of perceived paresthesia in the anodic paresthesia map and a body region of pain of the predetermined pain map. As shown in FIG. 10, the coverage scores 190 reflect the relative match between highlighted regions of each anodic paresthesia map for the electrodes E1-E8 against the highlighted region of the predetermined pain map 192. The coverage scores 190 for electrodes E4 and E5 are the highest since the regions of paresthesia most closely match the regions of pain in the predetermined pain map 192. The coverage scores 190 for electrodes E3 and E8 are the lowest since the regions of paresthesia hardly match the regions of pain in the predetermined pain map 192.

Figure 11:
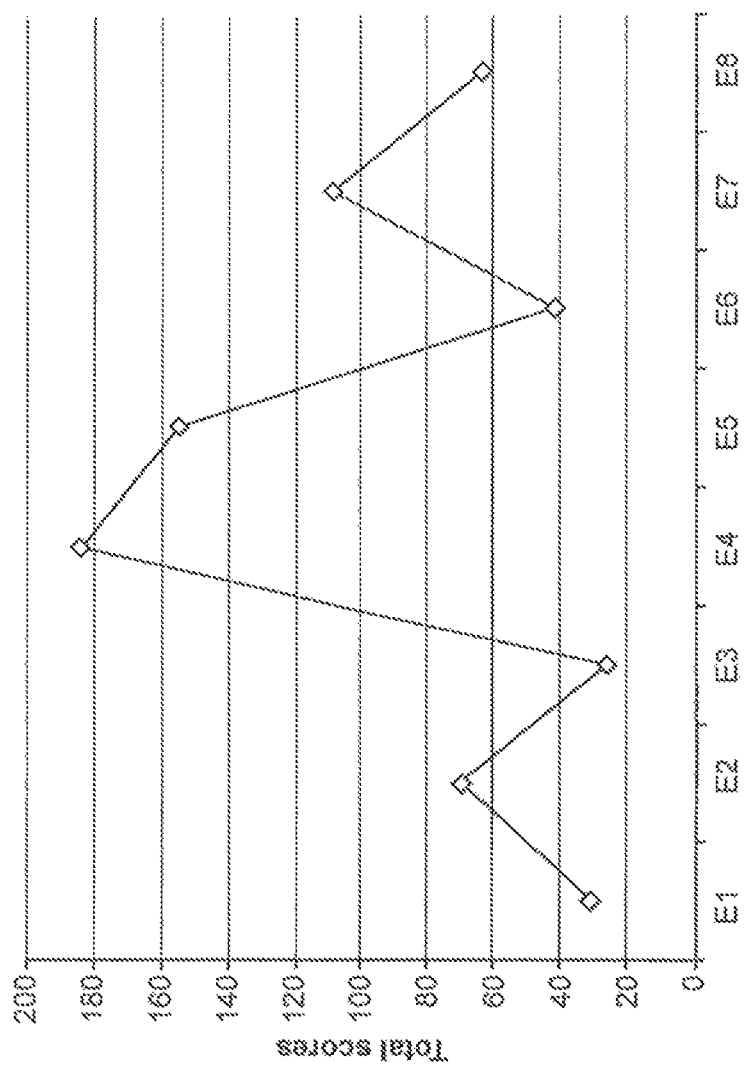
FIG. 11 is a plot of total scores computed by the CP of FIG. 1 for each of the electrodes.

Having calculated both the threshold scores 186 and coverage scores 190 for each of the electrodes 26, the controller 60 computes a total score for each of the electrodes 26. The CP 18 may be preprogrammed with algorithms that stipulate the weight for each part of the total score. For example, the threshold score and the coverage score of the paresthesia map may be given equal weight. In another example, the threshold score may be given two times more weight than the coverage score. In yet another example, the coverage score may be given two times more weight than the threshold score. For example, in FIG. 11, total scores for electrodes E1-E8 are represented graphically, depicting the highest total scores for electrode E4 (assuming equal weight is given to the threshold score and the coverage score). Therefore, in the automatic mode, the controller 60 automatically selects electrode E4 as the effective electrode.

Figure 12:
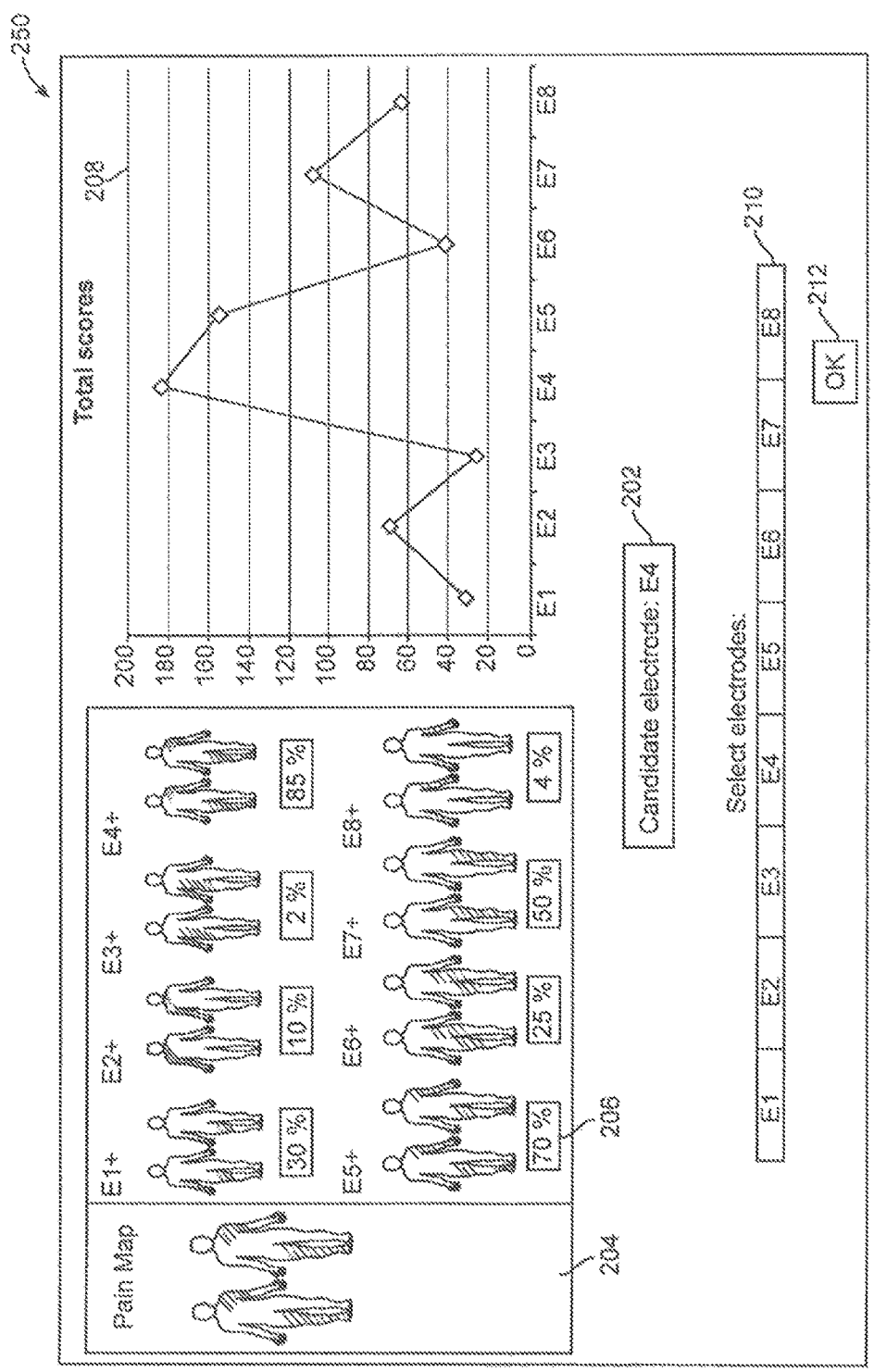
FIG. 12 is a plan view of a user interface of the CP of FIG. 6 in a semi-automatic electrode selection mode.

Referring now to FIG. 12, when the "Semi-Automatic" button 184 is selected, the user is taken to a semi-automatic electrode selection screen 250. In the semi-automatic mode of electrode selection, the user is guided into selecting one (or more) effective electrodes for sub-threshold modulation therapy.

In the preferred embodiment, similar to the automatic mode, total scores are computed for each electrode of the electrodes 26. However, instead of automatically selecting the electrode for sub-threshold modulation therapy the electrode is instead suggested as a candidate electrode for sub-threshold modulation therapy. As will be described below, in addition to suggesting a candidate electrode, total scores and paresthesia maps for all the electrodes 26 are also displayed, based on which the user makes an informed decision in selecting one or more effective electrodes.

To this end, the semi-automatic electrode selection screen 250 includes a graphical anodic paresthesia map 204 that depicts the anodic paresthesia maps for each electrode against the predetermined pain map. The anodic paresthesia map 204 may also include graphical coverage scores 206, the coverage scores calculated based on the relative match between each anodic paresthesia map and the predetermined pain map.

The semi-automatic electrode selection screen 250 also includes a graphical total score panel 208 that depicts the total score of each electrode. In the illustrated embodiment, electrodes E4 and E5 are shown as having the highest total scores out of electrodes E1-E8. Since electrode E4 has the highest total score, electrode E4 is suggested as the candidate electrode 202.

The semi-automatic electrode selection screen 250 further includes a manual effective electrode selection panel 210 that enables the user to select the effective electrode(s) for sub-threshold modulation therapy by actuating any of the graphical electrodes of the electrode selection panel 210. In the illustrated embodiment, the user may either manually select electrode E4 as the effective electrode on the electrode selection panel 210, or may ignore the suggestion and choose any other electrode on the electrode selection panel 210. In an alternate embodiment, the user may select more than one effective electrode on the electrode selection panel 210. When selecting more than one electrode, the user may ensure that the electrodes are in proximity to each other such that the electrodes function as one anode. Selecting effective electrodes that are far away from each other may not be beneficial to the patient since the current at each these remote electrodes will not combine in an effective manner. The semi-automatic electrode selection screen 250 also includes an "OK" button 212 that may be actuated after the user has selected the effective electrode(s). Selecting the "OK" button 212 takes the user back to the manual programming mode screen 100 of FIG. 7.

In an alternate embodiment, the semi-automatic electrode selection screen 250 may simply display the anodic paresthesia map 204 and the total score panel 208, and allow the user to select the effective electrode(s) on the electrode selection panel 210 based on user discretion without presenting the candidate electrode.

Figure 13:
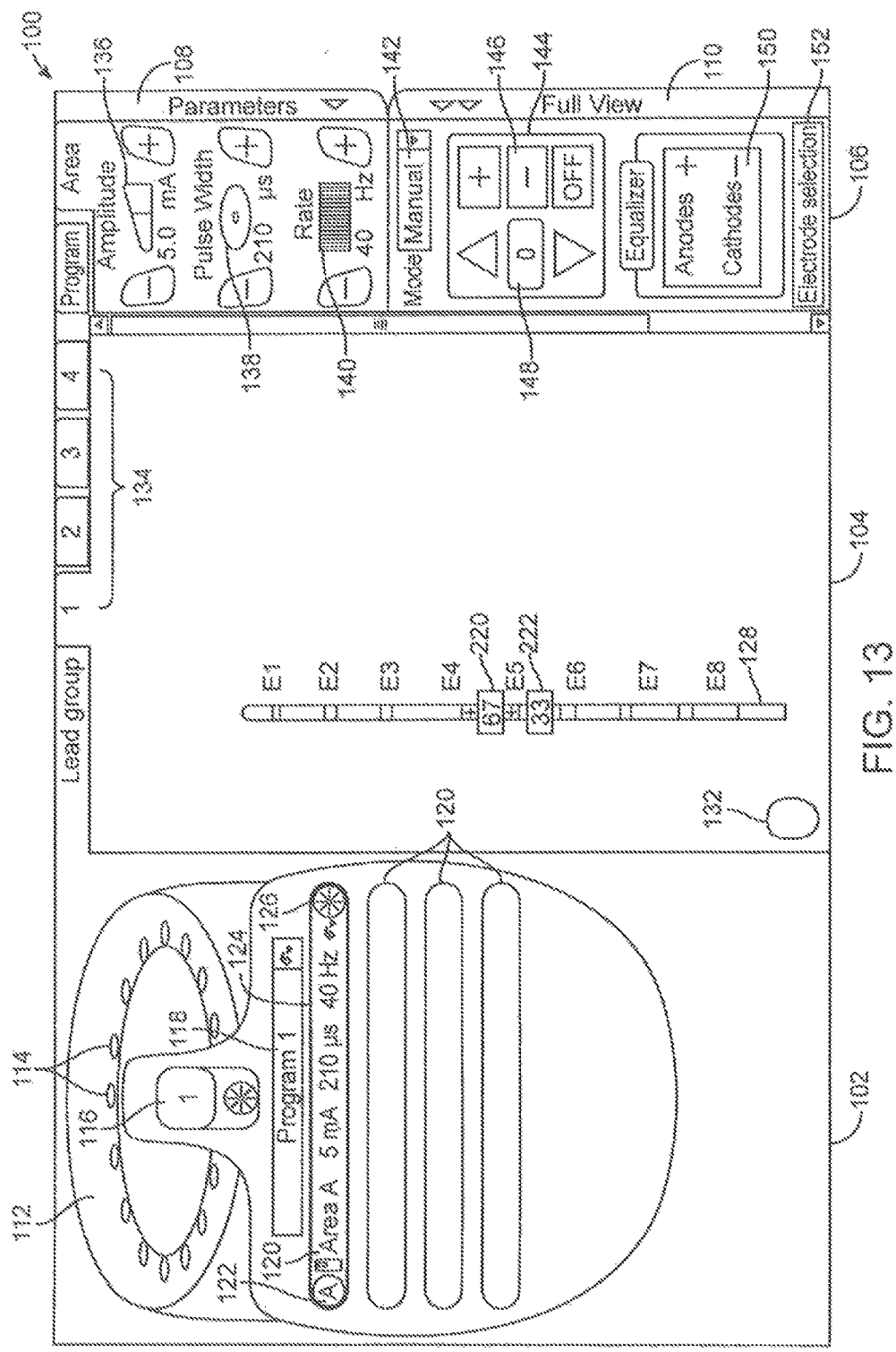
FIG. 13 is a plan view of a user interface of the CP of FIG. 6 for programming IPG of FIG. 3 in the manual programming mode.

Referring now to FIG. 13, once the effective electrode(s) have been selected (through either the automatic mode or the semi-automatic mode), the user is taken back to the manual programming screen 200, and the effective electrodes are automatically populated in the lead display panel 104 and are configured as anodes. In the illustrated embodiment, both electrodes E4 and E5 are selected (presumably through the semi-automatic mode), and are both configured as anodes. The controller 60 is configured for computing a distribution of sub-threshold electrical energy between the effective electrode(s) based on either a ratio of the anodic perception thresholds of the effective electrodes or a ratio of the cathodic perception threshold of the effective electrodes. For example, if there is only one effective electrode selected, 100% of the anodic electrical current will be allocated to the one effective electrode. If more than one effective electrode is selected, the electrical energy is automatically distributed based on the ratio. For example in FIG. 13, electrode E4 is allocated twice as much anodic electrical current as electrode E5, presumably mirroring a ratio of the underlying perception thresholds of electrodes E4 and E5. As shown in FIG. 9, the anodic perception threshold of electrode E4 (4.1 mA) is twice the anodic perception threshold of electrode E5 (2.1 mA). Since the ratio of the anodic perception thresholds of E4 and E5 is 2:1, two-thirds of the anodic current (67%) is allocated to E4 and one third of the anodic current (33%) is allocated to E5. Thus, in distributing the electrical energy based on the ratios of the anodic and/or cathodic perception thresholds, the controller 60 maintains an efficient functioning of the electrodes while delivering sub-threshold modulation energy to the effective electrodes.

It should be appreciated that the user may manually alter the distribution of current between the effective electrode(s) by using the amplitude control 148 that has arrows to increase or decrease the magnitude of the fractionalized current of the selected electrodes 220 and 224.

To deliver sub-threshold electrical energy to the effective electrode(s), the user may use amplitude adjustment control 136, pulse width adjustment control 138 and pulse rate adjustment control 140 to vary the modulation parameters as desired. While delivering sub-threshold modulation therapy, the modulation parameters are typically operated within a sub-threshold range (e.g., electrical pulse trains having a frequency greater than 1500 Hz and a pulse duration lower than 200 μs). As described above, in response to the adjustment of any of electrical pulse parameters via manipulation of the graphical controls in the parameter adjustment panel 106, the controller 60 generates a corresponding modulation parameter set (with a new pulse amplitude, new pulse width, or new pulse rate) and transmits it to the IPG 14 via the telemetry circuitry 54 for use in delivering the modulation energy to the electrodes 26. Although the sub-threshold pulse trains may be either cathodic or anodic, the present discloses focuses on delivering anodic sub-threshold electrical energy either in the form of a monophasic anodic pulse train or a biphasic pulse train that has an active anodic (positive) phase and a passive cathodic (negative) recharge phase.

The user may then define or select a sub-threshold modulation program using the program selection panel 102 of the manual programming screen 100 to deliver sub-threshold electrical energy to the patient. In particular, the user may browse through the carousel 112 for sub-threshold modulation programs and may select a suitable program.

Although the previous embodiments have focused on selecting single electrode(s) from the electrodes 26, it should be appreciated that an electrode set may comprise either a single electrode (as was the case in the illustrated embodiments), or a combination of electrodes. When the electrode set is a combination of electrodes, one combination of electrodes from multiple combinations of electrodes is selected for delivering sub-threshold modulation therapy to the patient. To provide effective therapy, electrode combinations typically comprise electrodes that are adjacent to each other. For example, the user may want to select the most effective electrode combination out of electrode combination A (electrodes E2 and E3), electrode combination B (electrodes E3 and E4) and electrode combination C (electrodes E4 and E5). In such a case, perception thresholds are determined and paresthesia maps are created for respective electrode combination A, electrode combination B, and electrode combination C, out of which the most effective electrode combination is selected to deliver sub-threshold modulation therapy.

Figure 14:
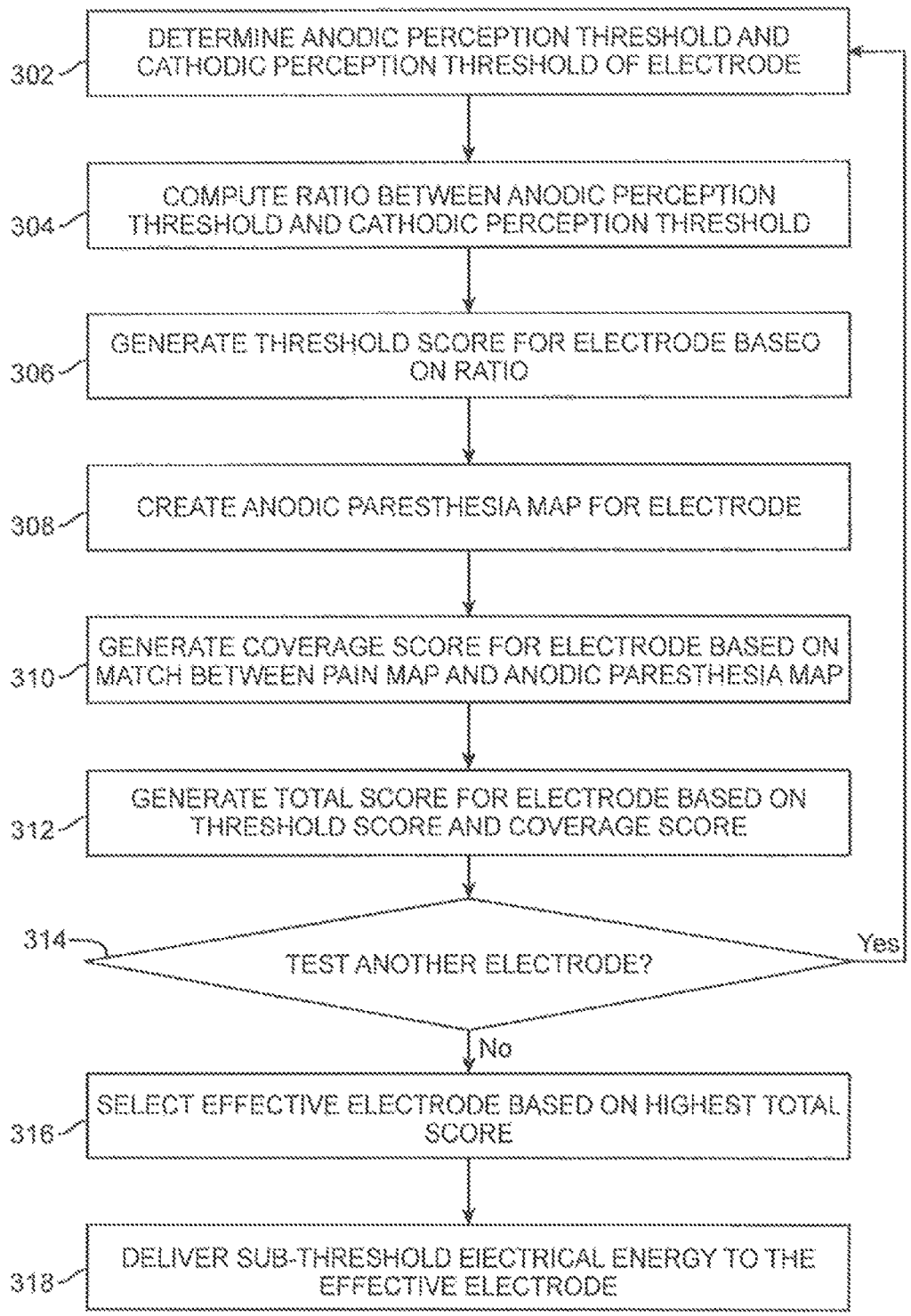
FIG. 14 is a flow diagram illustrating a technique used by the SCM system of FIG. 1 to select effective electrode(s) from the electrodes of FIG. 1.

Having described the structure and function of the SCM system 10, one exemplary technique of selecting the effective electrode(s) will be described with respect to FIG. 14.

The SCM system 10 determines an anodic perception threshold of super-threshold electrical energy delivered from an electrode (step 302). The SCM system 10 also determines a cathodic perception threshold of super-threshold electrical energy delivered from the electrode (step 304). Next, the SCM system 10 computes a ratio between the anodic perception threshold and the cathodic perception threshold for the electrode (step 306), and generates a threshold score based on the ratio between the anodic perception threshold and the cathodic perception threshold being closest to unity (step 308). The SCM system 10 also creates an anodic paresthesia map for the electrode (step 310), and generates a coverage score based on a relative match between a predetermined pain map and the anodic paresthesia (step 312). Based on the threshold score and the coverage score, the SCM system 10 generates a total score for the electrode (step 314). If there are additional electrodes to be tested, the system 10 goes through additional iterations of the process until total scores have been generated for all the electrodes (step 316). Otherwise, the system 10 selects an effective electrode based on a highest total score of the effective electrode in comparison with the any remaining electrodes (step 318). Once the effective electrode has been selected, the SCM system 10 delivers sub-threshold electrical energy from the effective electrode (step 320).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of neuromodulation, the method comprising:
   determining a ratio between an anodic perception threshold and a cathodic perception threshold for each of a plurality of electrode sets;
   selecting an effective electrode set from the plurality of electrode sets based on the ratios; and
   providing sub-threshold modulation therapy to a patient, including delivering sub-threshold electrical energy from the effective electrode set.

2. The method of claim 1, wherein the selecting the effective electrode set includes selecting an electrode set with the ratio between the anodic perception threshold and the cathodic perception threshold closest to unity.

3. The method of claim 1, wherein the patient suffers from pain in a body region, the method further comprising creating a paresthesia map comprising a body region of perceived paresthesia resulting from delivery of a super-threshold electrical energy from each of the electrode sets, wherein the selecting the effective electrode set includes selecting the effective electrode set using the paresthesia map.

4. The method of claim 3, wherein the selecting the effective electrode set includes selecting the electrode set corresponding to the body region of perceived paresthesia that matches the body region of pain.

5. The method of claim 4, further comprising determining a coverage score of a relative match between each body region of perceived paresthesia and the body region of pain, wherein the selecting the effective electrode set includes selecting the effective electrode set based on the coverage score.

6. The method of claim 5, further comprising determining a total score from the ratio and the coverage score for each of the electrode sets, wherein the selecting the effective electrode set includes selecting the one electrode set having a highest total score.

7. The method of claim 1, wherein the delivering sub-threshold electrical energy includes delivering a signal having a frequency greater than 1500 Hz.

8. The method of claim 1, wherein the delivering sub-threshold electrical energy includes delivering pulses having a pulse duration less than 200 μs.

9. The method of claim 1, wherein the delivering sub-threshold electrical energy includes delivering an electrical pulse train.

10. The method of claim 9, wherein the delivering the electrical pulse train includes delivering a biphasic pulse train.

11. The method of claim 10, wherein the delivering the biphasic pulse train includes providing an active anodic phase.

12. The method of claim 1, further comprising selecting another one of the electrode sets as another effective electrode set based on the ratios, wherein the providing sub-threshold modulation therapy includes delivering sub-threshold electrical energy from the other effective electrode set to the patient.

13. The method of claim 12, further comprising distributing the sub-threshold electrical energy among the effective electrode set based on the ratio.

14. The method of claim 1, further comprising determining the anodic perception threshold of super-threshold electrical energy respectively delivered from each of the plurality of electrode sets; and
determining a cathodic perception threshold of the super-threshold electrical energy respectively delivered from each of the electrode sets.

15. The method of claim 1, further comprising delivering super-threshold anodic electrical energy and super-threshold cathodic electrical energy from each of the electrode sets, sensing evoked compound action potentials (eCAPs) in response to the delivery of the super-threshold anodic electrical energy and the super-threshold cathodic electrical energy from each of the electrode sets, and storing the anodic perception threshold and cathodic perception thresholds in response to the sensing of the eCAPs.

16. The method of claim 1, further receiving user input indicative of anodic perception thresholds and cathodic perception thresholds.

17. A non-transitory machine-readable medium including instructions, which when executed by a machine, cause the machine to:
determine a ratio between an anodic perception threshold and a cathodic perception threshold for each of a plurality of electrode sets;
select an effective electrode set from the plurality of electrode sets based on the ratios; and
provide sub-threshold modulation therapy to the patient, including deliver sub-threshold electrical energy from the effective electrode set.

18. The non-transitory machine-readable medium of claim 17, further comprising instructions, which when executed by the machine, cause the machine to distribute the sub-threshold electrical energy among the effective electrode set based on the ratio.

19. A neuromodulation system for use with a plurality of electrode sets, comprising:
modulation output circuitry configured to independently deliver super-threshold anodic electrical energy and super-threshold cathodic electrical energy from each of the plurality of electrode sets, and deliver sub-threshold electrical energy from an effective one of the plurality of electrode sets; and
control circuitry configured to select the effective electrode set from the plurality of electrodes sets based on a ratio between an anodic perception threshold and a cathodic perception threshold for each of a plurality of electrode sets.

20. The system of claim 19, wherein the control circuitry is configured to distribute the sub-threshold electrical energy among the effective electrode set based on the ratio.

* * * * *